US008865401B2

(12) United States Patent
Young et al.

(10) Patent No.: US 8,865,401 B2
(45) Date of Patent: Oct. 21, 2014

(54) PURIFICATION AND CONCENTRATION OF PROTEINS AND DNA FROM A COMPLEX SAMPLE USING ISOTACHOPHORESIS AND A DEVICE TO PERFORM THE PURIFICATION

(75) Inventors: Charles C. Young, Mount Airy, MD (US); Alex J. Proescher, Perry Hall, MD (US); Emily E. Smith, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 790 days.

(21) Appl. No.: 12/817,288

(22) Filed: Jun. 17, 2010

(65) Prior Publication Data

US 2010/0323913 A1    Dec. 23, 2010

Related U.S. Application Data

(63) Continuation-in-part of application No. 12/808,023, filed on Jun. 14, 2010.

(60) Provisional application No. 61/268,969, filed on Jun. 18, 2009, provisional application No. 61/248,988, filed on Oct. 6, 2009, provisional application No. 61/013,774, filed on Dec. 14, 2007, provisional application No. 61/027,518, filed on Feb. 11, 2008.

(51) Int. Cl.
*C12Q 1/68* (2006.01)
*G01N 33/559* (2006.01)
*C07K 1/26* (2006.01)
*C12Q 1/70* (2006.01)

(52) U.S. Cl.
CPC ............... *G01N 33/559* (2013.01); *C07K 1/26* (2013.01); *Y10S 435/973* (2013.01)
USPC .......................... 435/6.1; 435/973; 435/287.2

(58) Field of Classification Search
CPC ................................ C07K 1/26; G01N 33/559
USPC .......... 435/174, 5, 6.13; 506/9; 204/456, 549, 204/606, 645
See application file for complete search history.

(56) References Cited

U.S. PATENT DOCUMENTS

| 3,869,365 | A  | 3/1975  | Sunden         |
|-----------|----|---------|----------------|
| 3,948,753 | A  | 4/1976  | Arlinger       |
| 4,897,169 | A  | 1/1990  | Bier et al.    |
| 5,447,612 | A  | 9/1995  | Bier et al.    |
| 5,464,515 | A  | 11/1995 | Bellon         |
| 5,817,225 | A  | 10/1998 | Hinton         |
| 6,685,813 | B2 | 2/2004  | Williams et al.|
| 6,780,584 | B1 | 8/2004  | Edman et al.   |
| 7,214,299 | B2 | 5/2007  | Armstrong      |
| 7,316,771 | B2 | 1/2008  | Weber          |
| 7,371,533 | B2 | 5/2008  | Slater et al.  |
| 7,399,394 | B2 | 7/2008  | Weber          |
| 7,473,551 | B2 | 1/2009  | Warthoe        |
| 7,494,577 | B2 | 2/2009  | Williams et al.|
| 7,517,442 | B1 | 4/2009  | Champagne      |
| 2002/0199094 | A1 | 12/2002 | Strand et al. |
| 2004/0031683 | A1 | 2/2004  | Eipel et al.  |
| 2004/0060821 | A1 | 4/2004  | Williams et al.|
| 2005/0170362 | A1 | 8/2005  | Wada et al.   |
| 2006/0078998 | A1* | 4/2006 | Puskas et al. ............. 436/64 |
| 2007/0158193 | A1* | 7/2007 | Burgi et al. .............. 204/452 |
| 2008/0197019 | A1 | 8/2008  | Santiago et al. |
| 2008/0237044 | A1 | 10/2008 | Fiering et al. |
| 2009/0032401 | A1 | 2/2009  | Ronaghi et al. |
| 2009/0139867 | A1 | 6/2009  | Marziali et al. |
| 2009/0178929 | A1 | 7/2009  | Broer et al.  |
| 2011/0097718 | A1* | 4/2011 | Nissum ..................... 435/6 |

FOREIGN PATENT DOCUMENTS

| EP | 05076569.2      | 1/2007 |
| WO | WO 2007/008064  | 1/2007 |
| WO | WO 2008/025806  | 3/2008 |
| WO | WO 2008/053047  | 5/2008 |
| WO | WO 2008/082876  | 7/2008 |

OTHER PUBLICATIONS

Zsolnai et al in "Agarose electrophoresis of DNA in discontinuous buffers, using a horizontal slab apparatus and a buffer system with improved properties" (Electrophoresis, Mar. 1993 vol. 14, No. 3, pp. 179-184).*
Shackman et al in "Gradient Elution Isotachophoresis for Enrichment and Separation of Biomolecules" (Anal Chem 2007 vol. 79, pp. 6641-6649, published online Aug. 4, 2007).*
Hirokawa et al in "I. Verification of bidirectional isotachophoresis and simultaneous determination of anionic and cationic components" (Journal of Chromatography, 1993: vol. 633, pp. 251-259).*
US 7,247,224, 7/2007, Weber. (withdrawn).
Baumann, G. et al., Gram-preparative Protein Fractionation by Isotachophoresis: Isolation of Human Growth Hormone Isohormones, Proc. Natl. Acad. Sci. USA, 73(3): 732-736, 1976.
Bottcher A. et al. Preparative Free-Solution Isotachophoresis for Separation of Human Plasma Lipoproteins: Apolipoproteins and Lipid Composition of HDL Subfractions, J. Lipid Res. 41:905-915, 2000.
Dolnik, V. et al. Capillary Electrophoresis on Microchip, Electrophoresis, 21(1):41-54, 1999.
Khurana, T. et al., Effects of Carbon Dioxide on Peak Isotachophoresis: Simultaneous Preconcentration and Separation, Lab Chip, 9:1377-1384 (Mar. 2009).
Lin, C-C et al., Integrated Isotachophoretic Stacking and Gel Electrophoresis on a Plastic Substrate and Variations in Dynamic Range. Electrophoresis 29(6) : 1228-1236, (Mar. 2008).

(Continued)

*Primary Examiner* — Catherine Hibbert
(74) *Attorney, Agent, or Firm* — Noah J. Hayward

(57) ABSTRACT

A method of simultaneously co-purifying and concentrating nucleic acid and protein targets is described. The method includes automation of the entire sample preparation process, performed by having an analyst add a sample into a device that performs all of the steps necessary to prepare a sample for analysis. The method provides for samples that are not split during the sample preparation process and where common purification methods can be used for purifying multiple analytes.

7 Claims, 10 Drawing Sheets

(56) References Cited

OTHER PUBLICATIONS

Shackman, J. et al., Gradient Elution Isotachophoresis for Enrichment and Separation of Biomolecules, Anal. Chem., 79(17): 6641-6649, (Aug. 2007).

Xu, Z., et al., High-Sensitivy Capillary and Microchip Electrophoresis Using Electrokinetic Supercharging Preconcentration: Insight into the Stacking Mechanism via Computer Modeling, J. Chromatography A, 1216(4):659- (Jan. 2009).

C. Blessum, et al., "Capillary electrophoresis : principles and practice in clinical laboratory," Annales de Biologie Clinique, vol. 57, No. 6, pp. 643-657, France, Nov. 1999 (with English abstract).

Takeshi Hirokawa, et al., "High-sensitive analysis by capillary electrophoresis and microchip electrophoresis using on-line preconcentration methods," The Japan Society for Analytical Chemistry, Bunseki Kagaku, vol. 52, No. 12, pp. 1069-1079, Japan, Jul. 2003 (with English abstract).

* cited by examiner

| Dilution factor | BG no purification | BG with purification | EH no purification | EH with purification |
|---|---|---|---|---|
| Neat | 0 | 17.94 | 0 | 32.27 |
| 1:10 | 25.12 | 21.28 | 44.08 | 35.95 |
| 1:00 | 28.45 | 24.9 | 39.86 | 39.94 |
| 1:000 | 29.53 | 28.7 | ND | ND |

PURIFICATION AND CONCENTRATION OF PROTEINS AND DNA FROM A COMPLEX SAMPLE USING ISOTACHOPHORESIS AND A DEVICE TO PERFORM THE PURIFICATION

CROSS REFERENCE TO RELATED APPLICATIONS

This application is a continuation-in-part of U.S. patent application Ser. No. 12/808,023, filed Jun. 14, 2010, which is a §371 of PCT/US2008/065260, International Filing Date of Jul. 18, 2008, and claims priority to U.S. Provisional Application Nos. 61/013,774, filed Dec. 14, 2007, 61/027,518, filed Feb. 11, 2008, 61/268,969, filed Jun. 18, 2009 and 61/248,988, filed Oct. 6, 2009.

GOVERNMENT INTERESTS

Certain research which gave rise to the present invention was supported by Department of Homeland Security Grant or Contract Number 2007-st-061-000003-02. Consequently, the government may retain certain rights in the invention.

BACKGROUND

1. Field of the Invention

This invention relates to a method of purifying proteins and nucleic acids

2. Background of the Invention

One of the largest contributors to false positive and false negative results in rapid detection technologies is inconsistent, variable processed samples. Sample preparation represents a critical, yet under developed capability. Present day sample preparation is usually performed manually. When automated, sample preparation involves mechanizing manual processing methods resulting in large, complex, robotic systems with significant reagent/waste streams and consumable usage.

Generic methods for the purification of DNA from cells or mixtures of cells have been available for many years and include alcohol precipitation, silica binding, standard gel electrophoresis methods, and phenol/chloroform extraction. The polymerase chain reaction (PCR), through its use of primers to amplify and detect regions of the previously-purified nucleic acid specific for different classes of organisms. The ability to develop generic purification methods for nucleic acids is due largely to the fact that all nucleic acid molecules are similar in chemical structure and these similarities can be taken advantage of when developing purification methods. However, most of these methods are time consuming and must currently be performed manually.

Proteins, on the other hand, are very different in structure from one type of protein to the next. Therefore, protein purification has largely focused on separation methods based on unique protein characteristics such as differences in size, charge, hydrophobicity, isoelectric point, antibody binding and/or enzyme-substrate specificities. When a number of these methods are performed in tandem eventually leads to a protein that has been purified away from all other proteins in the starting mixture. Typically, separation methods include chromatography electrophoresis, immunoprecipitation and magnetic separation techniques and the like. Chromatography is performed using columns which are typically quite large and require expensive equipment to obtain and analyze the samples. Therefore, methods currently used to purify nucleic acids are not used to purify protein and conversely, methods used to purify protein are not used purify nucleic acids.

U.S. Pat. No. 7,473,551 B2 (Warthoe) includes a microsensor and a hydrogel to isolate target analytes using a non-fluorescent detection system, which includes the target analytes as being nucleic acids or proteins. U.S. Pat. No. 7,371,533 discusses a method of separating polypeptides or polynucleotides using electrophoresis. U.S. Application No. 2009/0178929 (Broer et al.) discusses a device for isoelectric focusing for the separation of DNA or proteins. U.S. Application No. 2009/013986 A1 (Marziali and Whitehead) discusses methods and an apparatus for concentrating RNA or DNA. U.S. Application No. 2008/0237044 A1 (Fiering and Keegan) discusses a method and apparatus for continuously separating or concentrating molecules that include flowing two fluids in laminar flow through an electrical field and capturing at one of three outputs a fluid stream having a different concentration of molecules. Isotachophoresis is not disclosed in any of the applications, nor is the use of TAPSO buffer.

Isotachophoresis is a technique used to separate charged particles using a discontinuous electrical field to create sharp boundaries between the sample constituents. In this method, the sample is introduced between a fast leading electrolyte and a slow moving electrolyte to create a window between which a subset of constituents from a complex matrix can be segregated from other matrix constituents. The segregation occurs after application of an electrical field to the sample and the electrolytes are allowed to separate by charge. The electrolytes used for a separation are selected experimentally so that as many contaminating constituents as possible are excluded from the final sample.

Isotachophoresis is currently used in the field of protein purification as one potential method in capillary electrophoresis for the separation of specific proteins from a mixture of proteins. However, one disadvantage of isotachophoresis in capillary use is that one can only purify either negative or positively charged ions in the capillary tubes because these moieties will migrate in different directions upon application of the electrical field. The most common use of isotachophoresis is in protein stacking gels where protein samples are added to a gel in a wide band for separation by molecular weight. However, before separation by molecular weight can occur, the protein must be concentrated into a small band to increase resolution.

U.S. Pat. No. 3,869,365 (Sunden) is drawn to a broad method of counter-flow isotachophoresis comprising two electrolytes and the flow and voltage adjusted to maintain the sample at a desired position in the column. U.S. Pat. No. 3,948,753 (Arlinger) is drawn to an apparatus for isotachophoresis comprising a column, capillary tube, a detector, and a shunt tube bifurcating the column. U.S. Pat. No. 6,685,813 B2 (Williams et al.) is drawn to a method of separating components using isotachophoresis. U.S. Appl. No. 2004/0060821 A1 (Williams et al.) is drawn to a method of separating components using isotachophoresis. U.S. Pat. No. 7,494,577 B2 and U.S. Application No. 2004/0060821 (Williams et al.) discusses a method of separating components by loading a microchannel with a sample, placed between a trailing-edge electrolyte and a leading-edge electrolyte using isotachophoresis. There is no disclosure of the separation of either nucleic acids or proteins or to a TAPSO buffer. Application No. WO 2008/025806 (Gerhard Weber) is directed to a method of separating particles using electrophoresis and discloses isotachophoresis. Baumann, G. and Chrambach, A. disclosed the use of isotachophoresis for the isolation of hormones. (*Proc. Natl. Acad. Sci. USA*, 73(3): 732-736, (1976)). Böttcher, A. et al. disclosed preparative isotachophoresis for separation of human plasma lipoproteins, apolipoproteins and HDL subfractions, (*J. Lipid Res.* 41:905-915, (2000)). None disclose the simultaneous separation and purification of both nucleic acids and proteins. U.S. Appl. No. 2004/0031683 A1 (Eipel el al.) is drawn to a method of fractionating proteins using several procedures, including isotachophoresis. The two-step process includes capillary electrophoresis, but does not disclose the separation of nucleic acids. U.S. Pat. No. 7,399,394B2 (Gerhard Weber) is directed to a free flow electrophoresis (FFE) (also known as carrierless electrophoresis or isotachophoresis) method and related devices. U.S. Pat. No. 5,817,225 (Hinton) is drawn to an electrophoresis unit comprising an anode compartment, a cathode compartment, a separation chamber and an electrolyte in said chamber with an electrophoretic mobility between the mobilities of the nucleic acids and organic salts which are to be separated.

The separation of proteins was not disclosed. U.S. Pat. Nos. 7,316,771 B2 and 7,247,224 (withdrawn) (both by Gerhard Weber) is directed to a medium for electrophoresis comprising at least two acids and at least two bases as buffers. Neither disclose the separation of nucleic acids or proteins. U.S. Pat. No. 6,780,584 B1 (Edman et al.) is broadly drawn to a device with a first buffer reservoir containing a first buffer with a differing conductances, a conductive semipermeable matrix, and a first and second electrode and a specific binding entity and discloses a device which separates nucleic acid and RNA in hybridization reactions, but not the separation of proteins. U.S. Pat. No. 5,464,515 (Belton) is drawn to a procedure for loading one of several biological samples on an electrophoresis slab support, but does not disclose the separation of nucleic acids. U.S. Pat. No. 7,214,299 B2 and US 2002/0148729 A1 (Armstrong) is broadly directed to the separation of microbes and cells using electrophoresis methods. U.S. Pat. No. 5,447,612 (Bier et al.) is directed to a buffering composition for electrophoresis methods, including TAPSO and EACA (epsilon-aminocaproic acid) as complementary buffer pairs and methods. comprising the buffer composition in an isoelectric focusing method ,used with a recycling focusing instrument of the '169 Bier patent. 2008/0197019 A1 (Santiago and Khurana) discloses a method of using an electric field to isolate proteins and nucleic acids. Isotachophoresis is not disclosed, nor is the use of TAPSO buffer. 2010/0029915 discloses automated methods to isolate proteins or nucleic acids comprising the use of BES buffer and does not mention ITP. Xu, ZQ et al., (*J. Chromatography*, A, 1216(4):659, (Jan. 2009)) discusses electrokinetic supercharging as a transient ITP including the separation of proteins and nucleic acids.

Appl. No. EP 05076569.2 (Stichting voor de Technische Wetenschnappen) is drawn to a device for separating particles and the use of isotachophoresis for the non-simultaneous separation of nucleic acids or proteins and the use of binding molecules. Blessum, C. et al. disclose capillary electrophoresis in the separation of proteins, nucleic acids and lipoproteins, and its use in isotachophoresis. (*Ann. Biologie Clinique*, 57(6):643-647 (1999) [French]). Blessum et al. do not disclose the simultaneous isolation of nucleic acids and proteins using isotachophoresis. Dolnik, V. et al. disclose capillary electrophoresis techniques and microchip technology which includes isotachophoresis, and current methods of separation of nucleic acids or proteins, but does not disclose simultaneous separation of nucleic acids and proteins (*Electrophoresis*, 21(1):41-54, (1999) [Abstract only]). PCT Application No. WO 2008/082876 A1 (Balgley) is directed to a method of separating DNA or protein from a heterogeneous biomolecular sample using isotachophoresis coupled with liquid column chromatography. PCT Application No. WO 2008/082876 A1 (Weber, Gerhard) is directed to an electrophoresis method comprising a spacer zone and also separating at least one analyte, including DNA, protein or protein complexes using isotachophoresis. PCT Application No. WO 2007/008064 A1 (Kohlheyer et al.) is directed to a device and use of the device for separating particles in a fluid sample utilizing free flow isotachophoresis; and a discussion of the separation of DNA and proteins, although there is no mention of simultaneous separation. U.S. Pat. No. 4,897,169 (Bier and Twitty) discloses isotachophoresis and an apparatus using TRIS and cacodylic acid as electrolyte components. Hirukawa, T. et al. discusses the use of ITP for the separation of DNA fragments and SDS-proteins, but not simultaneously. (*Bunseki Kagaku*, (Japanese language, Abstract and FIGS. 13 and 16) 52(12):1069-1079 (2003)). Khurana, T. K. et al. describe ITP separation of DNA and proteins (*Lab Chip*, 9:1377-1384 (March 2009)). U.S. Patent Publication No. 2009/0032401 A1 (Ronaghi, Khurana, and Santiago) discloses a method of using an electric field to isolate proteins and nucleic acids, concentrating and separating at least one directly undetectable analyte of interest and said at least two directly detectable spacer molecules into zones using isotachophoresis; the analytes can be DNA or RNA. Lin, C-C et al., discusses an integrated ITP-gel electrophoresis device and discusses the separation of DNA and protein molecules. (*Electrophoresis*, 29(6):1228-1236, (March 2008)). Shackman, J. G and Ross, D. discusses a capillary isotachophoresis method and discusses the separation of DNA or protein molecules (*Anal. Chem.*, 79(17):6641-6649, (August 2007)).

Newer, rapid, simpler methods of sample processing are required to support the next generation detection systems. The newer detection methods will have a heavier reliance on sample preparation for the generation of meaningful results. In addition, sample preparation methods will need to support numerous different detection systems and be capable of being integrated as part of a complete sample processing and detection system.

Therefore, there is currently a great need in sample processing methods that are fast, inexpensive, and are easy to perform, even by untrained, non-technical staff in a variety of disciplines including biodefense, food and water, agricultural, environmental, clinical testing, and the like.

SUMMARY OF THE INVENTION

The present invention is drawn to a method of simultaneously co-purifying and concentrating nucleic acid and protein targets into a single volume that can then be tested on a variety of sensor technologies. This method represents a simple system that is readily automated into a hand held, disposable device capable of being operated by unskilled operators in a field environment.

DETAILED DESCRIPTION OF THE INVENTION

Figure 1:
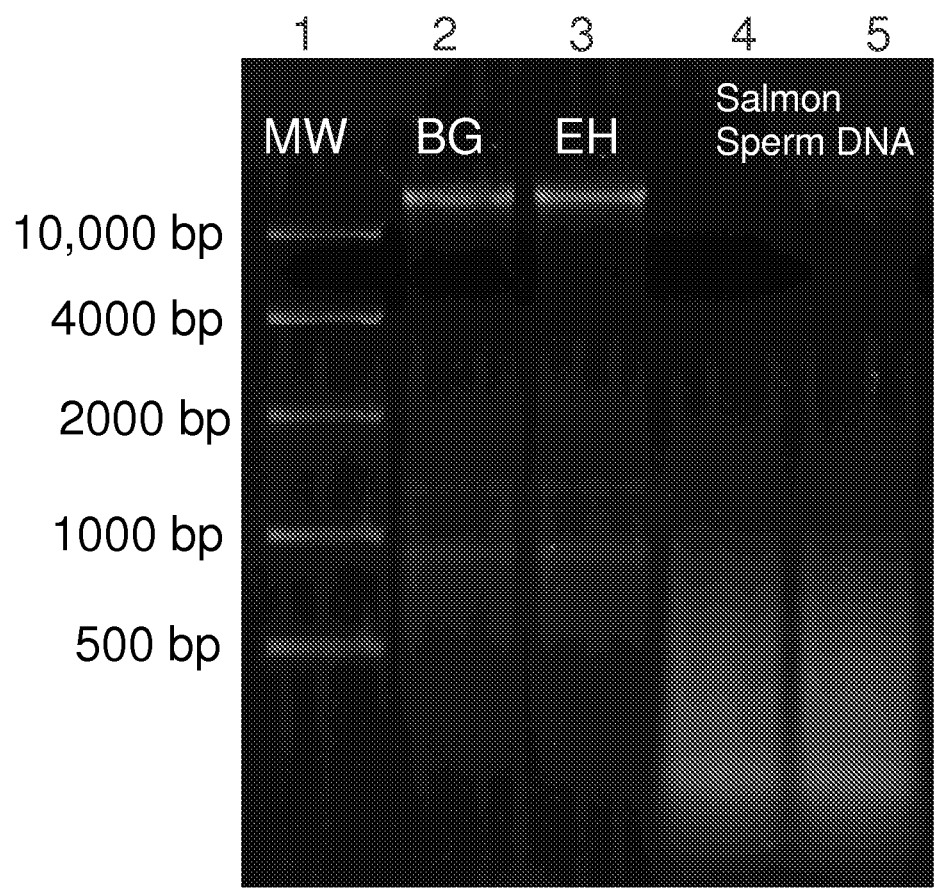
FIG. 1 depicts a standard 1% agarose submarine gel showing the relative mobility of genomic DNA isolated from *B. atrophaeus* (BG) and *E. herbicola* (EH).

The present invention is drawn to a method of simultaneously co-purifying and concentrating nucleic acid and protein targets into a single volume. The entire sample preparation process, regardless of the detection method can be automated using the invention. This automated sample preparation method is capable of having an analyst add a sample into a device that performs all of the steps necessary to prepare a sample for analysis. The present invention includes methods in which samples are not split during the sample preparation process and where common purification methods can be used for purifying multiple analytes. The sample processing methods of the invention are fast, inexpensive, and are easy to perform, even by untrained, non-technical staff in a variety of disciplines including biodefense, food and water, agricultural, environmental, clinical testing, and the like.

"Nucleic acid" molecules, as used herein include DNA, RNA, polynucleotides and oligonucleotides; synthetic or naturally-occurring. The nucleic acid molecules include any single-stranded sequence of nucleotide units connected by phosphodiester linkages, or any double-stranded sequences comprising two such complementary single-stranded sequences held together by hydrogen bonds. Unless otherwise indicated, each nucleic acid sequence set forth herein is presented as a sequence of deoxyribonucleotides (abbreviated A, G, C and T). However, the term "nucleic acid" includes a DNA molecule or polynucleotide, a sequence of deoxyribonucleotides, or an RNA molecule or polyribonucleotide. The corresponding sequence of ribonucleotides includes the bases A, G, C and U, where each thymidine deoxyribonucleotide (T) in the specified deoxyribonucleotide sequence is replaced by the ribonucleotide uridine (U).

Nucleic acids may originate in viral, bacterial, archobacterial, cyanobacterial, protozoan, eukaryotic, and/or prokaryotic sources. All DNA provided herein are understood to include complementary strands unless otherwise noted. It is understood that an oligonucleotide may be selected from either strand of the genomic or cDNA sequences. Furthermore, RNA equivalents can be prepared by substituting uracil for thymine, and are included in the scope of this definition, along with RNA copies of the DNA sequences isolated from cells or from virion particles. The oligonucleotide of the invention can be modified by the addition of peptides, labels, and other chemical moieties and are understood to be included in the scope of this definition.

Nucleic acid molecules detected or used by the methods or systems of the invention may also include synthetic bases or analogs, including but not limited to fluoropyrimidines, pyrimidines and purine nucleoside analogues include, fluoropyrimidines, including 5-FU (5-fluorouracil), fluorodeoxyuridine, ftorafur, 5'-deoxyfluorouridine, UFT, carboranyl thymidine analogues, FMAUMP (1-(2-deoxy-2-fluoro-D-arabinofuranosyl)-5-methyluracil-5'-monophosphate) and S-1 capecitabine; pyrimidine nucleosides, include deoxycytidine, cytosine arabinoside, cytarabine, azacitidine, 5-azacytosine, gencitabine, and 5 azacytosine-arabinoside; purine analogs include 6-mercaptopurine, thioguanine, azathioprine, allopurinol, cladribine, fludarabine, pentostatin, 2-chloroadenosine, AZT, acyclovir, penciclovir, famcyclovir, didehydrodideoxythymidine, dideoxycytidine, -SddC, ganciclovir, dideoxyinosine, and/or 6-thioguanosine, for example, or combinations thereof.

"Proteins" as used herein include peptides and polypeptides. A protein is a large molecule composed of one or more chains of nitrogen-containing amino acids linked together in a peptide linkage, in a specific order determined by the base sequence of nucleotides in the DNA coding for the protein. Examples of proteins include whole classes of important molecules, among them enzymes, hormones, antibodies and toxins. Proteins as used herein are composed of 20 standard amino acids, or may contain synthetic or naturally occurring non-standard amino acids. The amino acids present in the protein may be aromatic, D or L configuration, modified or having an R or S chirality. Such proteins may contain amino acids with posttranslational modifications. Such posttranslational modifications include but are not limited to carboxylation of glutamate, hydroxylation of proline or the addition of long hydrophobic groups can cause a protein to bind to a phospholipid membrane. Proteins may originate in viral, bacterial, archobacterial, cyanobacterial, protozoan, eukaryotic, and/or prokaryotic sources.

The proteins detected or used by the methods or systems of the invention include polypeptides and/or peptides and further include proteins that are part of a chimeric or fusion protein. Said chimeric proteins may be derived from species which include primates, including simian and human; rodentia, including rat and mouse; feline; bovine; ovine; including goat and sheep; canine; or porcine. Fusion proteins may include synthetic peptide sequences, bifunctional antibodies, peptides linked with proteins from the above species, or with linker peptides. Polypeptides of the invention may be further linked with detectable labels, metal compounds, cofactors, chromatography separation tags or linkers, blood stabilization moieties such as transferrin, or the like, therapeutic agents, and so forth. The proteins/peptides of the invention may originate in viral, bacterial, archobacterial, cyanobacterial, protozoan, eukaryotic, and/or prokaryotic sources.

Antibodies detected or used by the methods or systems of the invention include an antibody which is labeled with a labeling agent selected from the group consisting of an enzyme, fluorescent substance, chemiluminescent substance, horseradish peroxidase, alkaline phosphatase, biotin, avidin, electron dense substance, and radioisotope. The antibody of this invention may be a polyclonal antibody, a monoclonal antibody or said antibody may be chimeric or bifunctional, or part of a fusion protein. The invention further includes a portion of any antibody of this invention, including single chain, light chain, heavy chain, CDR, F(ab')2, Fab, Fab', Fv, sFv, dsFv and dAb, or any combinations thereof.

The invention is further drawn to an antibody-immobilized insoluble carrier comprising any of the antibodies disclosed herein. The antibody-immobilized insoluble carrier includes culture plates, culture tubes, test tubes, beads, spheres, filters, membranes, or affinity chromatography medium.

The invention also includes labeled antibodies, comprising a detectable signal. The labeled antibodies of this invention are labeled with a detectable molecule, which includes an enzyme, a fluorescent substance, a chemiluminescent substance, horseradish peroxidase, alkaline phosphatase, biotin, avidin, an electron dense substance, and a radioisotope, or any combination thereof.

The method of separation of the present invention may include separation medium including, agarose, polyacrylamide, mixed bed of agarose and polyacrylamide, starch, acrylamide-urea, and/or other separation media known in the art, in liquid, gel or membrane form, or a combination thereof. The separation may be done in slab electrophoresis units, columns, tubes, glass plates or slides, wells, membranes or the like.

At the present time, there are no rapid sample preparation methods, either manual or automated, that have demonstrated co-purification and concentration of both immunoassay protein targets and nucleic acid PCR targets in a single output.

One embodiment of the invention is a method and apparatus to simultaneously co-purify and concentrate nucleic acid and protein targets into a single volume that can then be tested on a variety of sensor technologies. In addition, this method represents a simple system that can be readily automated into a hand held, disposable device capable of being operated by unskilled operators in a field environment. The invention allows the purification of both nucleic acid and protein simultaneously using isotachophoresis. The sample is added to the middle of a device that allows isotachophoresis to occur in two directions toward both the positive and negative electrodes when a voltage is applied. A buffer system provides for "window DNA" moving toward the positive electrode and "windows" protein moving toward the negative electrode. Buffer conditions are chosen so that all proteins of interest would be positively charged to separate them from the DNA. If possible, the buffers are chosen to separate the proteins of interest from other contaminating proteins to increase the purity of the protein sample further.

Another aspect of the invention includes isotachophoretic purification and concentration of bacteria and viruses from complex samples. In many cases, the infectious dose of a bacteria or virus maybe as little as a single organism and that single organism may be present in a large volume of matrix. Because biological detectors can only test very small volumes, the typical strategy is to develop sampling plans in which only a statistical subset of each sample is tested. Therefore, a negative result only demonstrates that the sample subset that is tested is negative and does not mean that the entire sample is negative. The present invention allows a greater statistical probability that an entire sample is truly negative. The probability can be increased by testing more of the sample. Since the methods of the invention concentrate the organisms or target moieties present in a sample from the larger volume to a smaller volume, the probability of detection increases. Since bacterial cells and viruses have a net charge, they will also move in an electrical field. Therefore bacteria and viruses can be concentrated using the isotachophoretic method as described herein for nucleic acids and proteins. Since the isotachophoretic separation of bacteria and viruses or proteins and nucleic acids also purifies them from matrix components that could affect assay results, the resulting purification also allows more reproducible testing by molecular and immunoassays. It is envisioned that a system of the invention includes one or more cartridges that all run on a single, portable instrument. These cartridges could be disposable, re-usable or integrated into the system; and optionally could be interchangeable. To separate and concentrate bacteria and viruses in a sample matrix one disposable cartridge could be used; and the separation and purification of nucleic acids and protein, a different cartridge could be used.

The gold standard method for the detection of bacterial or viral pathogens remains culture-based even these methods are time consuming, typically requiring 1-2 days to make a final determination. A vast number of new, rapid detection technologies are poised to revolutionize the field of pathogen detection by delivering results in less than one hour, but they have been limited by significant false positive and false negative rates. One potential solution to decrease the numbers of false results generated is to fuse multiple disparate sensing technologies that provide truly orthogonal sensing capabilities. This type of approach is currently employed in a few cases where organisms are difficult or impossible to grow such as the detection of HCV virus in clinical settings where both immunoassay and PCR test results are used cooperatively in diagnosing disease. This approach has remained laboratory based due to the size and complexity of the equipment required for rapid detection approaches. However, more rapid and more sensitive technologies are currently being developed. A new generation of instruments will allow a paradigm shift in the way clinical and environmental diagnostics are performed because the technologies can be carried to the sample for testing as opposed to collecting the sample and taking it to the laboratory.

Sample preparation represents a critical, yet under-developed capability. One of the largest contributors to false positive and false negative results in rapid detection technologies is inconsistent, variably-processed samples. Therefore, there is a great need for the development of automated, rapid, reliable, and reproducible sample preparation methods. In most cases, present day sample preparation is performed manually and automation of sample preparation has involved mechanizing manual processing methods resulting in large, complex, robotic systems with significant reagent/waste streams and consumable usage. The present invention represents a newer, rapid, and simpler method of sample processing to support the next generation of detection systems which have an even heavier reliance on sample preparation for the generation of meaningful results. In addition, sample preparation methods of the invention is capable of standing alone to support numerous different detection systems and also is capable of being integrated as part of a complete sample processing and detection system. Sample preparation methods of the invention are also capable of purifying multiple analytes for detection to support an orthogonal sensing approach. The present invention avoids splitting a sample process on two different instrument systems, which can raise a number of issues regarding chain of custody requirements and sample consistency.

Detection methods for proteins include, but are not limited to: immunoassay, protein sequencing, mass spectrometry, functional assays that detect activity (such as enzymatic or protease assays), ligand binding but without the use antibodies, such as specific binding receptors, aptamers, gels, and/or combinations thereof. Detection methods for nucleic acids include, but are nucleotide limited to: PCR, isothermal amplification methods, hybridization reactions, microarrays, protein-DNA binding, mass spectrometry, gels, and/or combinations thereof. Oligonucleotides used in the systematic evolution of ligands by exponential enrichment (SELEX) are obtained from a random sequence library obtained from a combinatorial chemical synthesis of DNA. The oligonucleotide library is then screened for specific binding to target sequences for use as aptomers (U.S. Pat. Nos. 5,637,459, 5,475,096 and 5,270,163, all incorporated herein by reference).

In addition to sample preparation playing a vital role in the reproducibility of test results, the sample preparation methods of the present invention are applied to concentrate samples from large volumes. Sample concentration is an important step because most present day biological sensors require input volumes of less than 100 μL with PCR tests requiring as little as 1 μL. Microfluidic and chip-based approaches require sample sizes to be reduced even further into the submicron range. This reduction in input volume will result in a reduction in overall test sensitivity if analyte is not concentrated during the sample preparation procedure.

Another aspect of the invention is used in an application where concentration of all nucleic acids from a sample into a single aliquot would not be advantageous. Without being limited, the method of the invention can be used for nucleic acid sequence analysis of samples. It is anticipated that the invention can be used for the rapid identification of nucleic acid sequences, including, but not limited to bacterial or viral nucleic acid sequencing. It is anticipated that the inventive method will become the method of choice for rapid identification of bacteria and viruses from both clinical and environmental samples.

Traditionally, nucleic acid sequencing is a shotgun method whereby all nucleic acids in a sample are analyzed simultaneously regardless of the origin. Therefore, the most abundant types of nucleic acids in a sample will be identified and less abundant nucleic acids will be masked. In many types of samples it is this less abundant nucleic acids that are critical for identifying pathogens of interest. One of the biggest contributing factors for DNA that is present in large concentrations (masking DNA) is from human cells that are present in large quantities in many clinical sample types. The invention overcomes these drawbacks in traditional nucleic acid sequencing by removing human nucleic acids from a sample while purifying and concentrating bacterial and viral nucleic acids, is a significant step toward the application of nucleic acid sequencing and similar methods as a diagnostic tool. Under current systems, mitochondrial DNA comigrates with viral and bacterial nucleic acids. The method and apparatus of the invention includes the separation of mitochondrial DNA from bacterial and viral nucleic acids. In the isotachophoresis system of the invention, bacterial and viral nucleic acids are both purified and concentrated. However, small nucleic acids are not concentrated with the bacterial and viral nucleic acids because they migrate in the gel faster than the leading edge of the fast moving electrolyte. Therefore, while the method separates most nucleic acids by isotachophoresis, for small nucleic acids, there is a size separation component as well. Size is also a critical difference between human genomic nucleic acids and bacterial/viral nucleic acids in that human genomic DNA is much larger. The invention takes advantage of this size difference in the gel-based isotachophoresis format to simultaneously concentrate bacterial and viral nucleic acids while excluding human genomic nucleic acids based on size. One of the most important factors controlling the degree of migration possible in a gel electrophoresis format is the amount of cross linking in the gel, which is directly related to the concentration of agarose. Therefore, the cross-linking of the gel is set such that migration of large nucleic acids in the gel is prevented, but that smaller nucleic acid molecules are still able to enter the gel. Thus, bacterial and viral nucleic acids are purified and concentrated, while at the same time the bacterial and viral nucleic acids are separated from genomic nucleic acids.

Another aspect of the invention is a method, apparatus and kit which allows both DNA and protein to be concentrated separately so that each can be isolated independently. Additionally, the invention includes a method, apparatus and kit which allows for the simultaneous and independent isolation of species of proteins to be isolated simultaneously and independently from different species of nucleic acids.

Kits of the invention would include labelled reagents and instructions for use of such reagents either in combination with an included apparatus or with use of a separate apparatus.

WORKING EXAMPLES

Buffer Abbreviations: Bicine buffer, (N,N-Bis(2-hydroxyethyl)glycine), Bis-Tris (2-(bis(2-hydroxyethyl)amino)-2-(hydroxymethyl) propane-1,3-diol), TAPSO (2-Hydroxy-N-(tris(hydroxymethyl) methyl)-3-aminopropanesulfonic acid), HEPES (4-(2-hydroxyethyl)-1-piperazine ethanesulfonic acid), MES (2-(N-morpholino)ethanesulfonic acid).

Example 1

Purification and Characterization of Nucleic Acid

Methods:

*Bacillus atrophaeus* (BG) spores were prepared by adding 1 gram of a lyophilized spore stock to 1 mL of ddH2O. *Erwinia herbicola* (EH) cells were prepared by growing cells from a freezer stock to mid-log phase in nutrient broth. Cells were harvested by centrifugation suspended in ddH2O. BG spores and EH cells were lysed and their genomic DNA purified using the QIAMP DNA Mini Kit (PN 56304, Qiagen) according to manufacturer's instructions with minor modifications to the volumes and incubation times. Purified DNA was quantitated by OD260/280 ratios (Sambrook and Russell (2001), *Molecular Cloning: A Laboratory Manual*, 3rd edition, Cold Spring Harbor Laboratory Press) and previously validated in-house real time polymerase chain reaction assays (RT-PCR) targeting the recA gene of BG and the chorismate mutase (aroQ) gene of EH. Purified DNA was added directly to the standard humic acid solution prior to separation. DNA was diluted to a concentration in which there was not enough DNA present to reproducibly generate a positive PCR reaction (endpoint).

Characterization of Proteins

Proteins for this study were chosen to represent a broad range of molecular weights and isoelectric points. Purified proteins including ovalbumin, bovine serum albumin, horse radish peroxidase, and lysozyme were purchased from Sigma-Aldrich Corporation. All proteins were diluted to standard concentrations of 1 mg/mL (wt/vol) in Bis-tris MES buffer.

Buffer Formulations

All buffers for the isotachophoresis experiments were prepared to final concentrations based on empirical experimental results as described below. Higher or lower concentrations can be used for isotachophoresis based on the amount of material being separated and the degree of separation required. Buffers were allowed to remain at the pH obtained from the dilution of the material into double-distilled deionized water (ddH$_2$O).

Agarose Gel Electrophoresis

Standard submarine agarose gels were prepared using 1% Agarose MP (Roche Applied Science) in 0.5× tris-borate-EDTA buffer (Bio-Rad Laboratories).

Agarose Gel Isotachophoresis

Agarose gel electrophoresis was performed using a standard agarose gel electrophoresis unit (Bio-Rad Laboratories) except the gel was run as a sea level gel as opposed to a submerged gel. All gels were prepared using 1% wt/vol MP agarose, because this was the lowest concentration of agarose that provided a gel that was rigid enough to handle without tearing. However, concentrations between 0.5-1.5% were tested and determined to be acceptable. Even broader ranges of agarose concentrations could be used as long as the agarose concentration was high enough to form a crosslinked gel and low enough to allow migration of large molecular weight bacterial genomic DNA into the gel.

For all isotachophoresis experiments, 1% agarose gels were prepared using 0.4 M Bis-tris and 0.1 M MES. Gels were poured directly on the surface of the electrophoresis unit as opposed to the gel tray that was provided. This allowed a complete seal on the sides and bottom of the gel to isolate the anode and cathode buffer chambers. The gel comb was modified by taping the teeth of the comb to form a single, long well to allow a larger sample volume ranging from 800 microliters (µL) to 1 mL to be separated. The comb was placed into the gel approximately 1 inch from the cathode edge. Two different buffers were used to fill anode and cathode buffer reservoirs. The cathode buffer consisted of 0.2 M Bicine and 0.1 M NaOH and the anode buffer consisted of 0.4 M BisTris and 0.1 M acetic acid. Buffer was added to the reservoirs so that they were even with the top of the gel so that the two buffer systems remained separated throughout the run. Gels were run at 150 volts for approximately 4 hours for the nucleic acid and protein to be concentrated and purified.

To extract the DNA from the gel, a long well was cut in the gel directly in front of the dye line, using a razor blade. The well went all the way to the bottom of the gel and was slightly longer than the dye line. The well was filled with the BisTris MES buffer. Current was again applied to the gel and the dye moved into the cut well. Using a pipette, the liquid dye and DNA could be removed. This was normally done several times in order to remove all of the dye/DNA.

A variety of different buffer formulations were used in a gel-based isotachophoresis system to separate and concentrate nucleic acids and proteins. The combination that performed the best consisted of a Bis-tris MES solution in the gel, a Bicine/NaOH cathode buffer and a Bis-tris/acetic acid solution as the anode buffer. Therefore, this buffer system was used for further study into the feasibility of using an isotachophoretic method for simultaneous purification of nucleic acid and proteins. However, it should be noted that the method is not limited to these buffers alone and that further effort will yield buffer systems that perform similarly, or possibly even better. Therefore, the method is not limited specifically to the buffer system chosen for the experiments described below.

Figure 2:
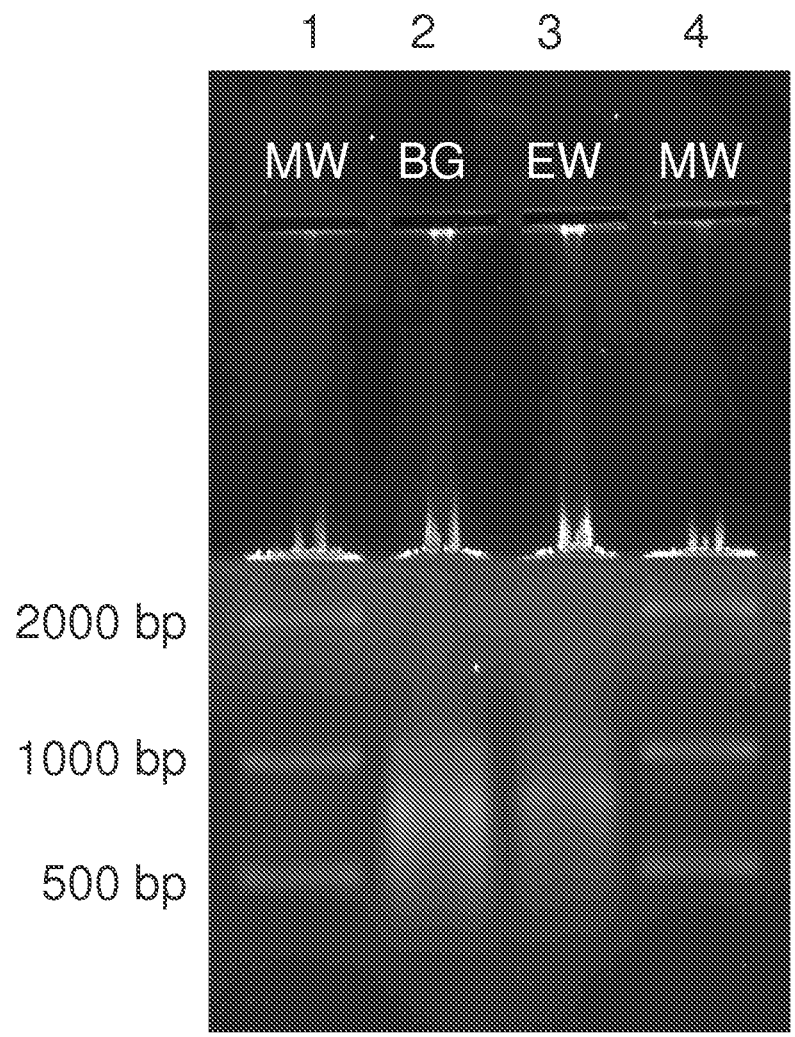
FIG. 2 shows a standard 1% agarose isotachophoresis gel showing the relative mobility of genomic DNA isolated from *B. atrophaeus* and *E. herbicola*.

DNA isolated from *Bacillus atrophaeus* (BG) and *Erwinia herbolitica* (EH) was purified and then separated by submarine agarose gel electrophoresis in order to determine the size and quality of the genomic DNA that was isolated (FIG. 1). In both instances genomic DNA can be observed in a band at a molecular weight of >10,000 base pairs with a few lighter bands at around 1000 base pairs. These lighter bands could represent either DNA from small plasmids present in the cell or genomic nucleic acids that have been degraded during the purification process. Molecular weight standards also separated on the gel according to their relative sizes as denoted FIG. 1 with larger pieces of DNA migrating less distance than smaller sized DNA. When the same isolated purified DNA was run on a sea level isotachophoretic gel, the large molecular weight bands of the molecular weight standards along with the BG and EH genomic DNA comigrated with the xylene cyanol dye between the leading edge of the Bicine buffer front (from the anode buffer chamber) and the trailing edge of the MES buffer (from the agarose gel; FIG. 2). DNA at molecular weights of approximately 2000 base pairs and below migrated through the gel at an equivalent or greater speed than the Bicine buffer front and therefore, these smaller molecular weight DNA molecules separated based on molecular weight and were not concentrated at the interface of the leading and trailing buffer components.

Figure 3:
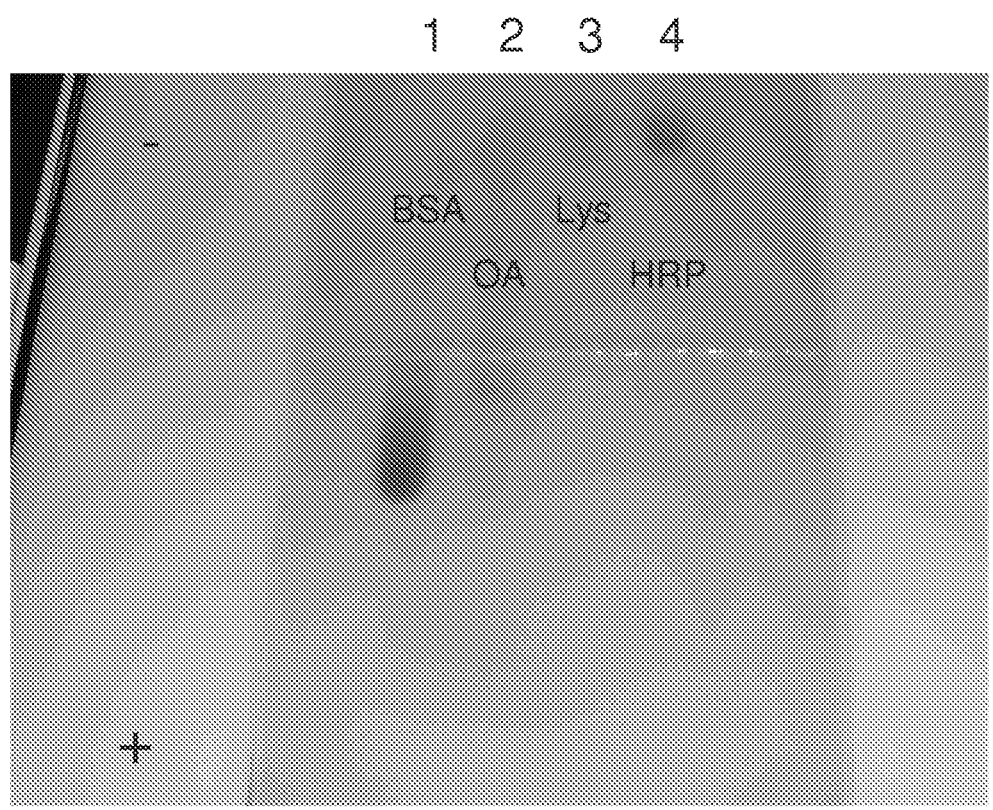
FIG. 3 shows a standard 1% agarose submarine gel showing the relative mobility of purified proteins.
Figure 4:
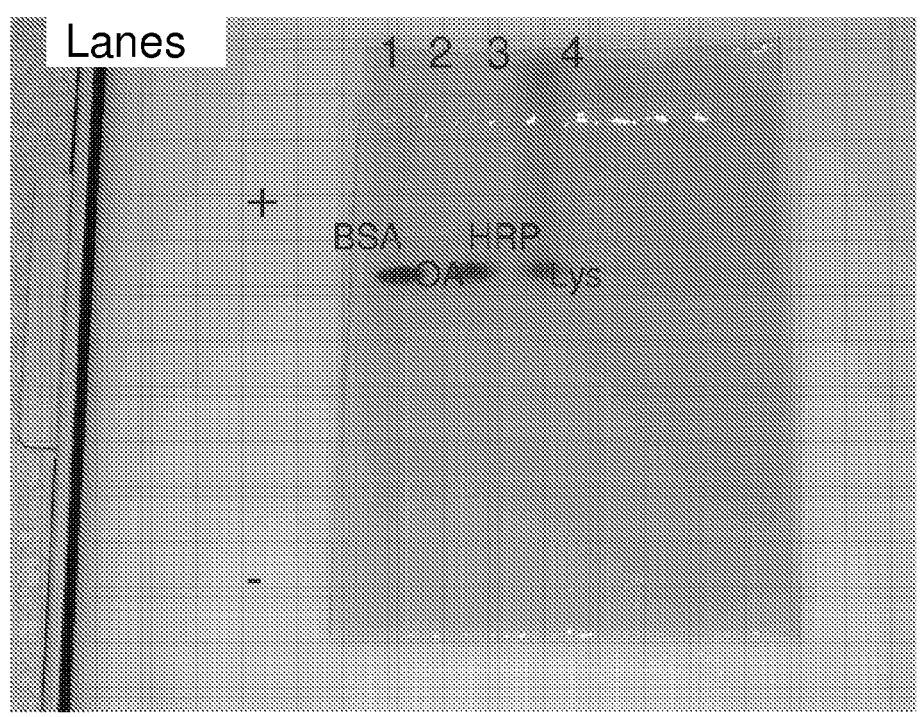
FIG. 4 depicts a standard 1% agarose isotachophoresis gel showing the relative mobility of purified proteins.

Purified proteins of various molecular weights and isoelectric points were purchased commercially and diluted to concentrations of 1 mg/mL in phosphate buffered saline. The proteins were then separated on a 1% agarose submarine gel with 0.5×TBE buffer which was identical to the gel used to separate DNA except for the proteins which were loaded in the middle of the gel as opposed to loading near the anode end of the gel. As can be seen in FIG. 3, two of the four proteins, BSA and ovalbumin, migrated toward the cathode while the other two proteins, lysozyme and horse radish peroxidase, migrated in the opposite direction toward the anode. Additionally, due to the fact that these proteins have mixed charges at pH 8.0, they do not migrate as discrete bands, but smear throughout the gel lane making characterization difficult. When the same four proteins were loaded onto an isotachophoretic gel identical to the gel run for the purification of DNA (FIG. 4), three of the four proteins including BSA, ovalbumin, and horse radish peroxidase all migrated toward the cathode. In addition, the three proteins comigrated with the xylene cyanol dye between the leading edge of the Bicine buffer front and the trailing edge of the MES buffer in the exact same position that the large molecular weight DNA and the xylene cyanol migrated in FIG. 2 above. The fourth protein, horseradish peroxidase, presumably moved in the opposite direction even in the isotachophoresis buffer system. It was not possible to move the protein starting locations to the middle of the gel in order to perform isotachophoresis due to the constraints of the buffer system, but had protein moved toward the cathode, it should have been seen by the dye staining.

Figure 5:
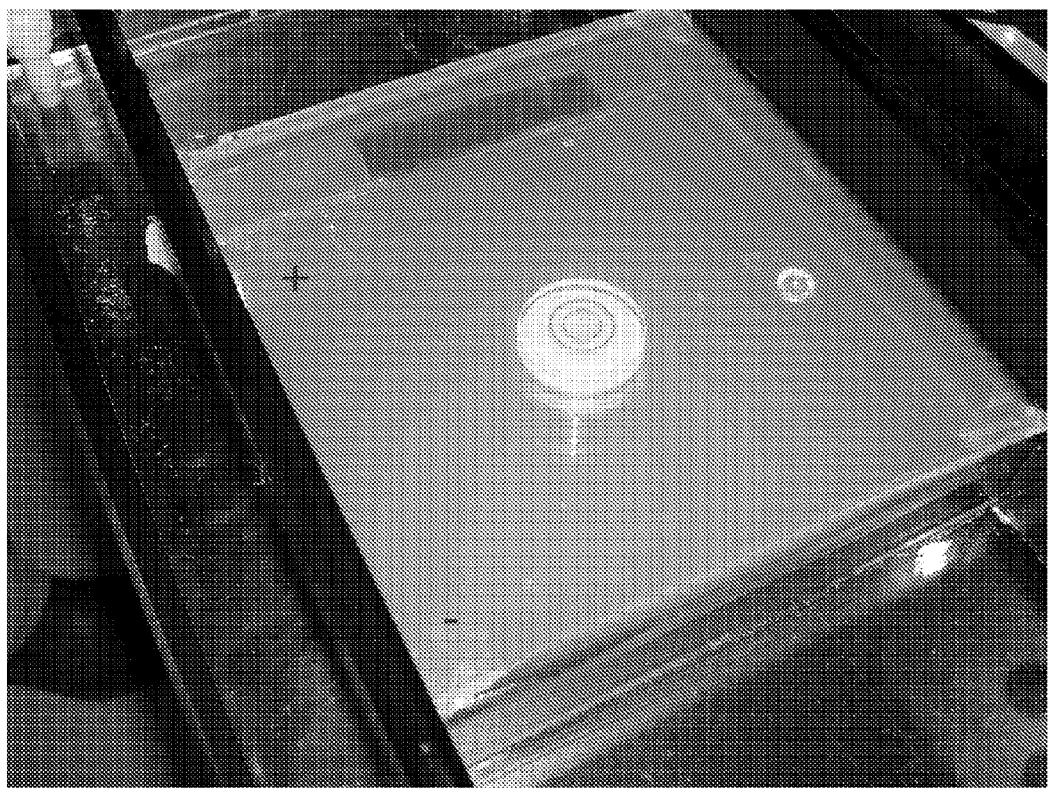
FIG. 5 shows an isotachophoresis gel prior to the application of voltage and showing the DNA, protein, xylene cyanol and humic acid combined and located within a single sample well and showing the dark color of the humic acids.

Once the relative mobilities of the bacterial genomic DNA and proteins were established on the isotachophoretic gel, proteins, DNA, and xylene cyanol were mixed with a standard concentration of humic acids that generated a reading of 1.0 at an optical density of 203.6 nm. This mixture was then separated on an isotachophoretic gel under identical conditions to the previous gels shown in FIGS. 2 and 4. Because the method not only separates humic acids from both nucleic acids and protein, but also concentrates nucleic acid and protein at a single location on the gel, extremely wide loading positions can be cut to increase the volume of material added to the gel. Increasing the volume of material that can be separated will greatly enhance the sensitivity of any test run on the purified material. The relative positions of the protein and large molecular weight DNAs were tracked according to the position of the xylene cyanol dye and migration of the humic acids were tracked according to their characteristic visible brown color in the gel. FIG. 5 shows a typical isotachophoresis gel in which protein, DNA, xylene cyanol, and humic acids were mixed, prior to application of voltage; and FIG. 6 shows the same gel after separation of protein, DNA, xylene cyanol, and humic acids by isotachophoresis.

Humic acid is a known inhibitor of the polymerase that is used to copy DNA in the PCR reaction. Isotachophoretic purification of DNA from humic acids improves performance of PCR detection methods. Pure *B. alrophaeus* and *E. herbicola* DNA was combined with the standard concentration of humic acid to generate a single sample for analysis. A portion of the sample was removed to represent an unpurified sample and the remaining solution was purified by isotachophoresis as described above. Sample was rescued from the gel by first allowing separation to occur, turning off power to the gel, and then cutting a small well into the gel between the leading edge of the DNA/xylene cyanol and the trailing edge of the humic acid. The newly created well was then filled with double distilled deionized water prior to restoring power to the gel. Once power was restored, the xylene cyanol band was tracked until it entered the well, at which time power to the gel box was stopped again and the xylene cyanol and DNA was removed with a pipette. A comparison of xylene cyanol concentrations based upon OD absorbance before and after isotachophoretic separation was used to determine the percent recovery of the sample. This percent recovery was then used to standardize the amount of solution added to the PCR reaction. Based on absorbance measurements, it was determined that recoveries of up to 95% with 40-fold concentration were possible even in this gel box-based system and even higher recoveries and greater sample concentration can be expected as application specific electrophoresis units are employed. Both purified and unpurified DNA was then tested neat, with a 1:10 dilution in $ddH_2O$, 1:100 dilution in $ddH_2O$, and a 1:1000 dilution in $ddH_2O$. In addition, the BG DNA was further diluted to 1:10,000 in $ddH_2O$ while EH DNA was not. The results (FIG. 8) show that the unpurified DNA without dilution could not be detected by PCR for either BG or EH due to failure of the reaction to amplify even after 45 cycles. However, DNA purified by isotachophoresis could be amplified readily with Ct values of 18 for BG and 32 for EH. As samples are diluted, PCR reaction inhibitors such as humic acids are present at lower concentrations allowing for more efficient amplification which would lead to lower CT values. However, the total amount of nucleic acid present is also diluted resulting in less nucleic acid to amplify, which leads to higher CT values. At some point, dilution of the humic acid inhibitor will reach the point that there is no longer inhibition of the polymerase and at that point, the Ct values of the purified and unpurified sample would be expected to be the same. For the BG assay this occurs at the 1:10,000 dilution and for the EH assay this occurs at the 1:000 dilution.

Purification

Figure 6:
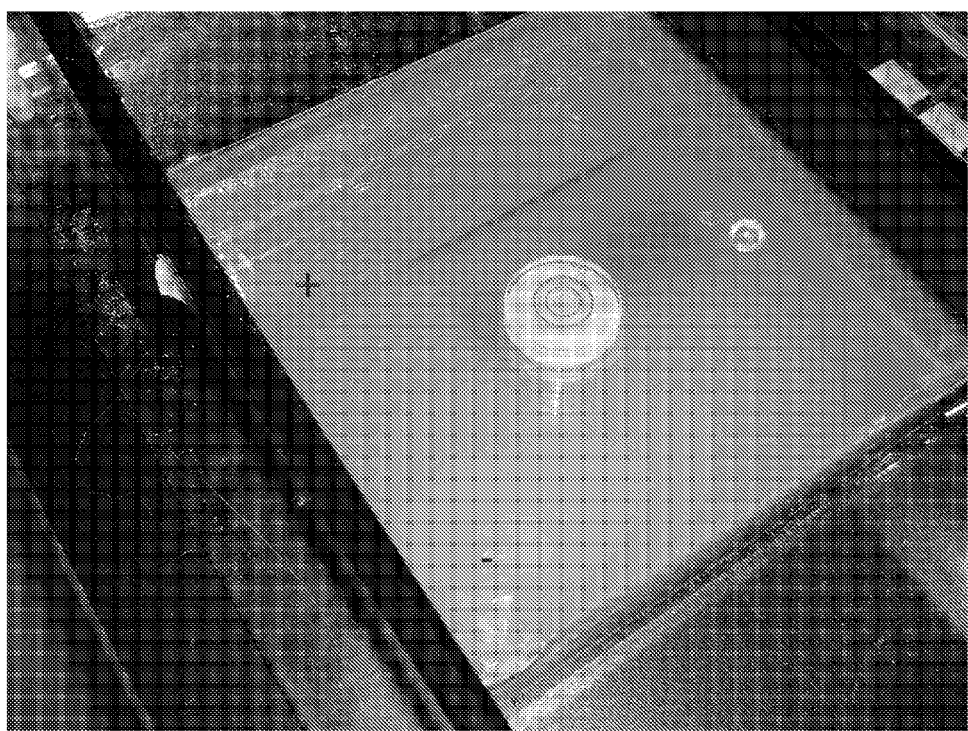
FIG. 6 demonstrates an isotachophoresis gel after the completion of the run showing the separated DNA, protein, and xylene cyanol dye concentrated into a thin band (blue) separated from the humic acids (brown) which are not concentrated by the system.

A mixture of *Bacillus atrophaeus* (BG) and *Erwinia herho/itica* (EH) genomic DNA; humic acid and purified proteins of various molecular weights and isoelectric points were separated on an isotachophoretic gel under specific conditions (FIG. 6). The Figure shows the DNA, protein, and xylene cyanol dye concentrated into a thin blue band at a single location on the gel, purified from the brown humic acids, which are not concentrated by the system. The leveling bubble that can be seen under the semi-transparent gel is not part of the actual separation process.

Recovery

The percent recovery of the sample was determined by comparing xylene cyanol concentrations based upon OD absorbance before and after separation. This percent recovery was then used to standardize the amount of solution added to the PCR reaction. Based on absorbance measurements, it was determined that recoveries of up to 95% with 40-fold concentration were possible even in this gel box-based system. Higher recoveries and greater sample concentration can be expected as application specific electrophoresis units are employed.

Amplification

Figures 7, 8:
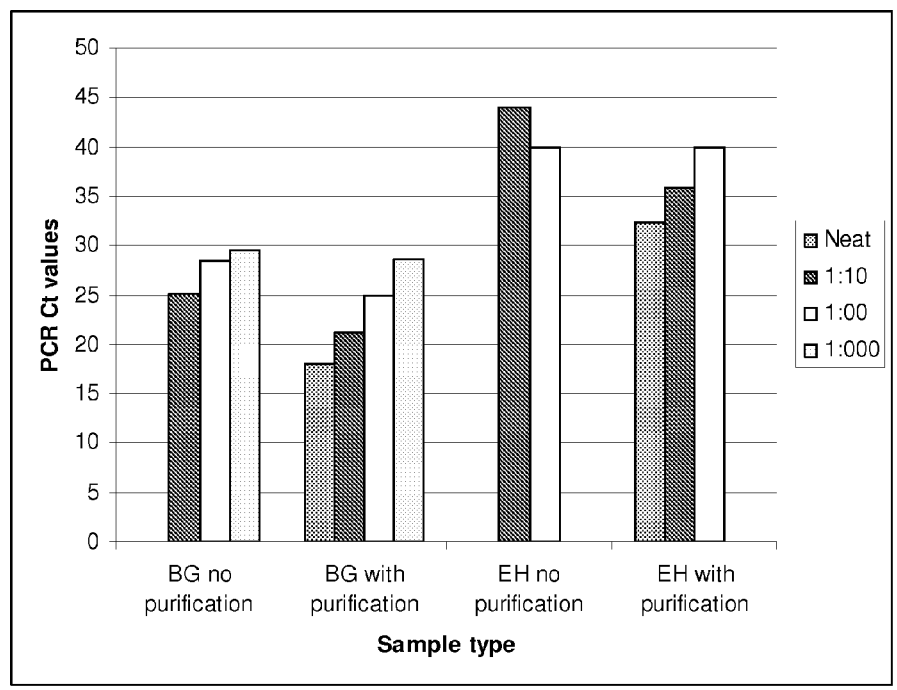
FIG. 7 is a graphic representation of Ct values of PCR reactions comparing the relative amplification of BG and EH DNA dilutions from samples containing humic acid and sample containing humic acid purified by isotachophoresis.
FIG. 8 shows the Ct values of PCR reactions comparing the relative amplification of BG and EH DNA dilutions from samples containing humic acid and sample containing humic acid purified by isotachophoresis.

Following purification from humic acid, bacterial genomic DNA was amplified by PCR. PCR threshold cycle (Ct) values were determined and compared to the Ct values of control samples that did not undergo the purification method of the invention (FIGS. 7 and 8).

Isotachophoretic Size Exclusion of Large Molecular Weight Nucleic Acids

Small nucleic acids were not concentrated with the bacterial and viral nucleic acids because they migrated in the gel faster than the leading edge of the fast moving electrolyte. Therefore, there was a size separation component as well. Size is also a critical difference between human genomic DNA and bacterial/viral nucleic acids in that human genomic nucleic acid is much larger. The concentration for cross-linking is adjusted according to the size of nucleic acid desired to be isolated.

Figure 9:
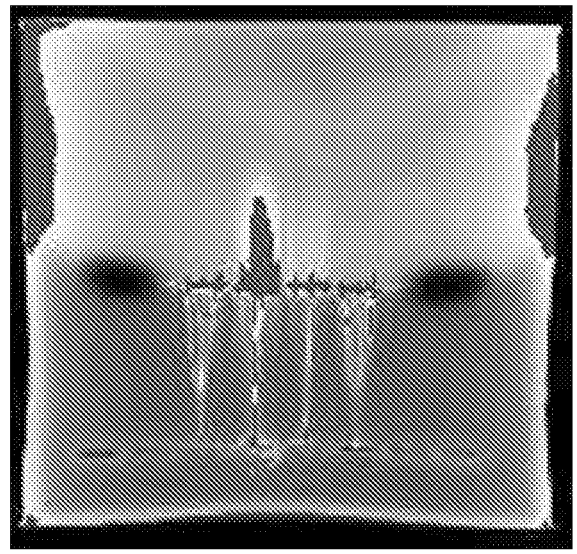
FIG. 9 depicts a 1% agarose isotachophoresis gel showing high and low molecular weight DNA ladders, and calf thymus DNA.
Figure 10:
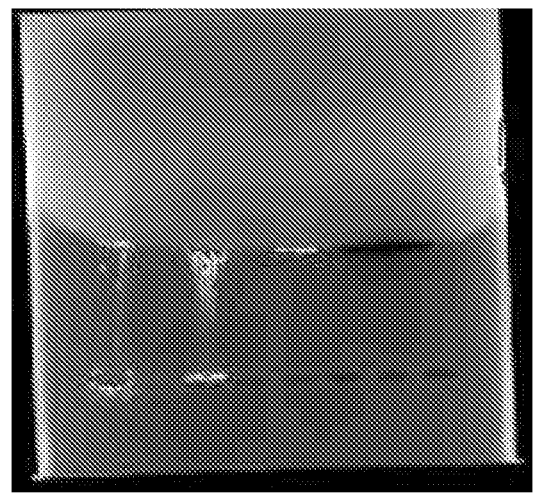
FIG. 10 depicts a 1% agarose isotachophoresis gel showing high and low molecular weight DNA ladders, and calf thymus DNA.

In order to test this hypothesis, calf thymus DNA was ordered from Sigma chemical company along with a high molecular weight DNA ladder. Traditionally, DNA ladders consist of DNA fragments of known sizes that can be run on a gel as a standard to estimate the molecular weight of an unknown nucleic acid tested in parallel. However, the ladder was used herein to test whether or not large nucleic acid molecules could be separated while at the same time concentrating nucleic acids with sizes in the molecular weight range of bacteria and viruses. The first experiment (FIG. 9) was performed according to the laboratory protocol described in the provisional patent in which a 1% agarose gel was prepared and run. The results of this experiment showed that most large molecular weight DNA (both calf thymus and the large molecular weight DNA ladder) entered the gel and concentrated with nucleic acid in the size range of bacteria and viruses. However, in a second experiment (FIG. 10), when a 2% agarose gel was tested under the same conditions the large molecular weight DNA remained in well and did not migrate into the gel. A portion of the large molecular weight DNA in the ladder entered the gel, but could not keep up with the moving buffer front. No equivalent-sized molecular weight DNA was observed in the calf thymus DNA sample. The calf thymus DNA sample did contain some DNA of the appropriate size that it concentrated in the same region that bacterial and viral nucleic acid would concentrate, but that might be removed by further optimizing gel concentrations to remove it. Regardless, this example demonstrated that significant amounts of large molecular weight nucleic acid could be separated from nucleic acid in a size range equivalent to bacteria and viruses by excluding the high molecular weight eukaryotic genomic nucleic acids from the isotachophoresis gel. Therefore, this provides a solution for the detection of bacteria and viruses using next generation detection approaches.

Example 2

Isotachophoresis agarose gels were prepared using the identical equipment described above except the buffers employed in the separation process were changed. Separation and concentration of protein and DNA was accomplished using TAPSO NaOH as a buffer in place of Bicine (FIG. 11) as well as a buffer system that separates and concentrates both nucleic acids and proteins using a dual buffer system (FIG. 12).

TABLE 1

TAPSO Buffer Run

1% Gel, (0.4M Bis-Tris, 0.05M MES)
0.301 g agarose
12 ml 1.0M Bis-Tris
3 ml 0.5M MES
15 ml filtered diH$_2$0
1.5 µl EtBr The gel solution above was prepared and poured into the gel box. Once solidified, the wells were loaded with 12 µl each of xylene cyanol dye, 500-10 Kb ladder standard, 7.24 µg/ul BG DNA, 1 mg/ml OVAL, 1 mg/ml BSA, and xylene cyanol dye. A TAPSO buffer (0.2 M TAPSO, 0.1 M NaOH) was added to the negative electrode side of the gel box and a Bis-Tris acetate buffer (0.4 M Bis-Tris, 6 mM acetic acid) was added to the positive electrode side of the gel box. The buffers were poured until they reached the top surface of the gel without flowing over the top of the gel. The gel was run at 25 V for 3.5 hours.

TABLE 2

TAPSO-Bicine Buffer Run

1% Gel, (0.4M Bis-Tris, 0.05M MES)
0.308 g agarose
12 ml 1.0M Bis-Tris
3 ml 0.5M MES
15 ml filtered diH$_2$0
1.5 µl EtBr A gel solution was prepared and poured into the gel box. Once solidified, the wells were loaded with 12 µl each of xylene cyanol dye, 500-10 Kb ladder standard, 7.24 µg/ul BG DNA (ran in 2 lanes), 1 mg/ml OVAL, 1 mg/ml BSA, and xylene cyanol dye. A TAPSO buffer (0.2 M TAPSO, 0.1 M NaOH) was added to the negative electrode side of the gel box and a Bis-Tris acetate buffer (0.4 M BisTris, 6 mM acetic acid) was added to the positive electrode side of the gel box. Buffers were poured until they reached the top surface of the gel without flowing over the top of the gel. The gel was run at 25 V for 30 minutes. The TAPSO buffer was then removed and replaced with a Bicine buffer (0.2 M Bicine, 0.1 M NaOH). The run continued at 25 V for another 2.5 hours.

Figure 11:
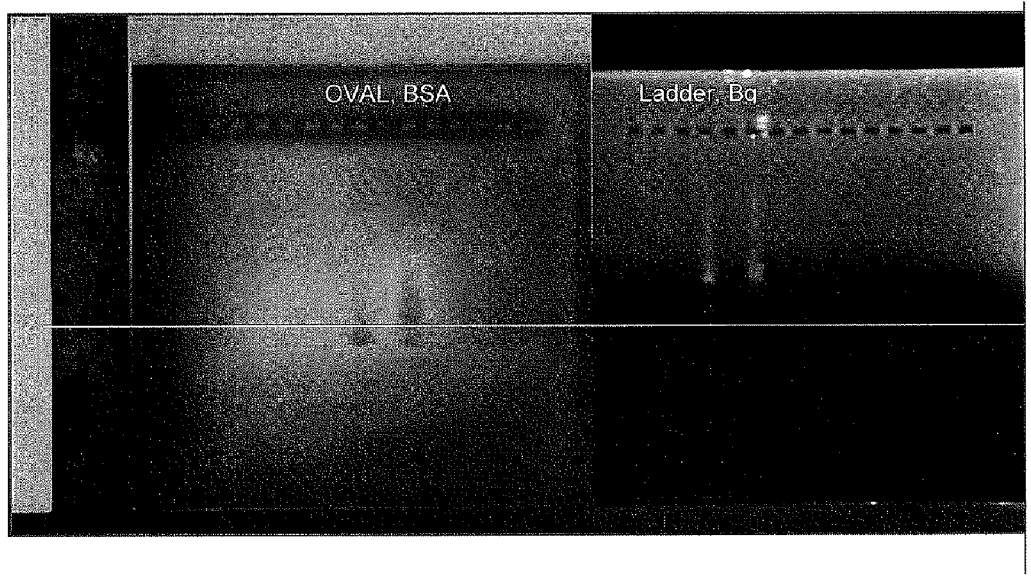
FIG. 11 shows a 1% isotachophoresis agarose gel run with proteins (left panel A) and DNA (right panel B). The gel was run using TAPSO NaOH/Bis-Tris MES/Acetic acid.
Figure 12:
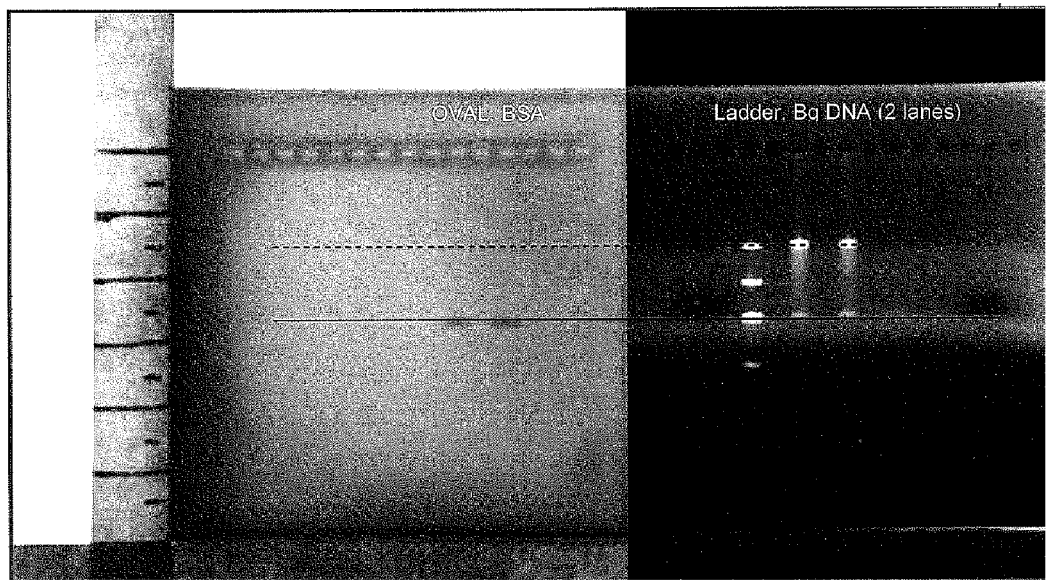
FIG. 12 shows a 1% istotachophoresis agarose gel run with proteins (left panel A) and DNA (right panel B). The gel was run using TAPSO NaOH/Bis-Tris MES/Acetic acid followed by the removal of TAPSO/NaOH and its replacement with Bicine in the buffer chamber, resulting in two buffer fronts.

FIG. 11 shows a clear spatial separation of the two proteins which ran at the TAPSO NaOH/Bis-Tris front (shown by the white line) from the DNA (BG), which ran above the buffer front. FIG. 12 shows a buffer system of TAPSO NaOH/Bis-Tris MES/Acetic acid which was run for the first 30 minutes of the run followed by the removal of TAPSO NaOH and its replacement with Bicine in the buffer chamber. This resulted in two buffer fronts. This gel showed clear spatial separation of the two proteins which ran at the TAPSO NaOH/Bis-Tris MES front (shown by solid line) from the DNA (BG) which ran at the Bicine/TAPSO NaOH front shown by the dashed line. These Figures clearly show that the TAPSO buffer system allows separation and concentration of nucleic acids and proteins to different locations so that they can be processed separately.

Example 3

Isolation of RNA and Proteins

293FT cells were grown overnight on supplemented DMEM culture media. The growth media was removed from the culture flask and the cells were washed twice with 10 mL of phosphate buffered saline (PBS). Cells were collected from the flask by scraping into a final volume of 1 mL of PBS followed by centrifugation at 1000×g for 5 minutes to pellet the cells. A 500 µL volume of lysis buffer was then added to the cells with mixing by gently repeatedly pipetting the cells. The cells were placed at −80° C. for 5 minutes followed by a 2 minute incubation in a 37° C. water bath. This freeze thaw procedure was performed 3 times. Cellular debris in the extract was then concentrated by centrifugation at 1000×g for 2 minutes and the supernatant was carefully transferred to a new tube and kept at 4° C.

RNA purification was performed using the ToTALLY RNA™ Kit from Ambion Inc. according to manufacturer's instructions. After extraction, the resulting pellet was suspended in RNA elution buffer and stored at −20° C. until used the following day.

Agarose gels were cast directly into MINISUB® gel GT gel boxes (Bio-Rad Laboratories) and wells were formed using a 15 well comb. Voltage applied to the gels was supplied from a BioRad Power Pac Universal. Gels were visualized using a VersaDoc gel imager in conjunction with the QUANTITY ONE® computer program, both from BioRad. Protein gels were photographed using a handheld Nikon E4300 camera.

Bicine buffer, TAPSO buffer, MES, sodium hydroxide, acetic acid, ethidium bromide xylene cyanol, coomassie blue, and methanol were all products of Sigma Aldrich. Agarose MP which is manufactured specifically for the preparation of low percentage gels allowing the separation of high molecular weight nucleic acids was purchased from Roche Diagnostics. The DNA ladder used was BioRad EZ LOAD™ HT Molecular Marker 500 bp-10 kb.

The Bicine anode buffer was comprised of 0.2 M Bicine and 0.1 M NaOH. A 200 mL volume of a 1.0 M Bicine stock solution and 100 mL of a 1.0 M NaOH stock solution were added to 700 mL of deionized water to produce one liter of buffer. The TAPSO anode buffer was comprised of 0.2 M TAPSO and 0.1 M NaOH. One liter of buffer was prepared by adding 400 mL of a 0.5 M TAPSO stock solution, and 100 mL of a 1 M NaOH stock solution to 500 mL of deionized water. The BisTris cathode buffer was 0.4 M Bis-Tris and 6 mM acetic acid and was prepared by adding 400 mL of a 1.0 M Bis-Iris solution and 6 mL of a 1.0 M Acetic Acid to 594 mL deionized water.

Gels were prepared in a solution containing 0.4 M Bis-Tris and 0.05 M MES. This buffer was prepared by combining 12 mL of a 1 M Bis-Tris stock solution, 32 mL of a 0.5 M MES stock solution, and 15 mL deionized water.

Figure 13:
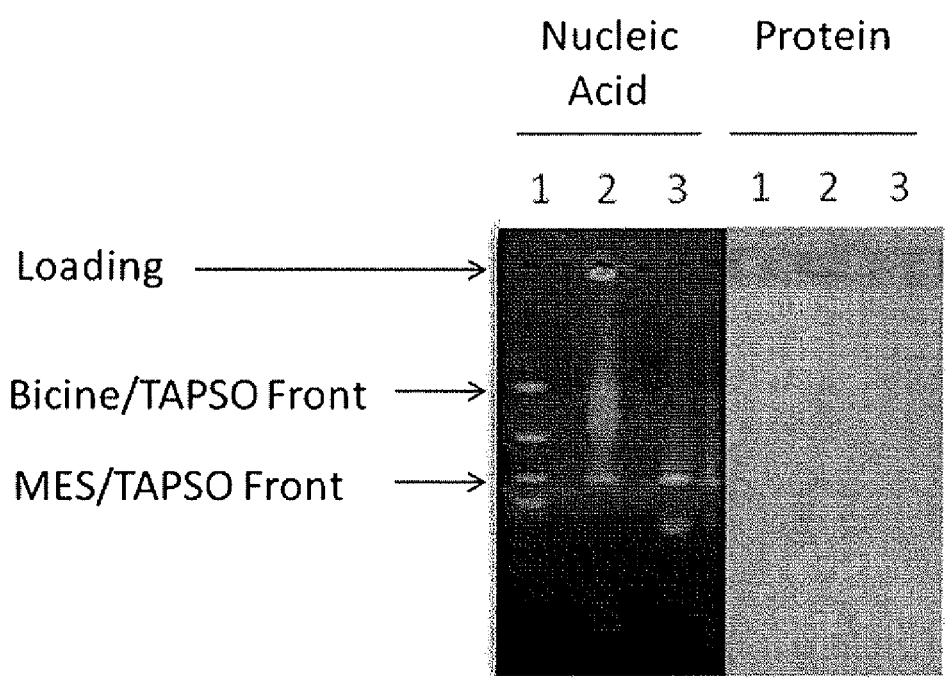
FIG. 13 depicts an isotachophoresis gel showing nucleic acids and proteins from a 293FT human cell extract and purified RNA from the same extract.

Gels were prepared by adding 0.3 g of agarose to 30 mL of BisTris MES buffer for a final gel concentration of 1% agarose (w/v). A 1.5 µL volume of an ethidium bromide stock solution was added to the gel to allow post-run visualization of nucleic acids. After gels were poured and hardened the anode and cathode buffers were added to the anode and cathode buffer chambers, respectively. Buffers were added so that their height was equal to the top of the gel, but did not spill over top of the gel. Therefore, the gel was run as a "sea level" gel as opposed to a submerged gel to prevent the anode and cathode buffers from mixing during the run. Cellular extracts and purified RNA concentrations were adjusted visually based on previous runs to yield a concentration that was easily distinguishable by visualization with a camera. These solutions were added to wells in the gel as shown in FIG. 13 and the top was placed onto the gel box. The electrophoretic separation was performed at 25 volts (9 milliamps) for 3.5 hours. The gels were run slowly to prevent heating which causes slight changes in anode buffer isoelectric points. In some applications gels have been run at 125 V for as short at 20 minutes and shown excellent separation. (It is expected that the invention would also include run times that could be decreased substantially by increasing the voltage for this application as well or by developing an apparatus specifically for this type of separation that would not require the use a conventional gel box.) After the run was complete, the gel was transferred to the VersaDoc gel imager for photographic documentation of nucleic acid content followed by transfer to an acetic acid fixative and coomasie blue staining for visualization of protein separation.

In a purely isotachophoretic approach the gel matrix itself would be poured at a low enough concentration that there would be no separation effect due to molecular size. However, even using gels that allow migration of high molecular weight DNA, the gels cannot be poured at a low enough concentration that would completely prevent molecular weight separation and at the same time allow the gels to be handled for visualization. Therefore, some degree of molecular weight separation in this system cannot be avoided.

Therefore the molecular weight separation was exploited to allow a dual separation common to 2-dimensional gel separation, but in only a single dimension. This allows the dual separation to be conducted simultaneously with no manual intervention, which is critical for the development of a rapid sample preparation cartridge for integration into an automated system or a stand-alone purification device.

The simultaneous dual separation approach allows benefits of both size and charge to be exploited along with the advantage of concentration gained by isotachophoresis. A number of different cross-linking percentages were investigated it has been determined that by altering gel concentration different size ranges of nucleic acids can be "windowed out", while concentrating all nucleic acids that separate within that window to a single location. FIG. 13 shows an isotachophoresis gel with separated nucleic acids and proteins from a 293FT human cell extract (lane 2) and purified RNA from the same extract (lane 3). Lane 1 contains molecular weight markers.

In the gel that was run in FIG. 13, a 1% agarose MP concentration was used, although other gel concentrations could also be used. Lane 2 contained the 293FT cell extract without purification. In this instance, the agarose cross-linking in the gel prevented genomic DNA from entering the gel matrix and it remains near the loading location. Near the center of the gel are 2 bands that is possibly due to mitochondrial DNAs. Mitochondrial DNA is roughly the size of a bacterial genome and it has been demonstrated previously, using a slightly different isotachophoretic approach that these bands, along with microbial genomes, can be concentrated and purified into a single location on the gel. Finally, cellular RNAs are concentrated at the TAPSO/MES buffer front. In order to prove that the material at the TAPSO/MES buffer front was indeed cellular RNAs, a portion of the identical cell extract shown in lane 2 was extracted for total RNA and the resulting purified RNA (lane 3) was run side by side with the cell extract. The resulting purified RNA ran to the identical location of the presumed RNA from the cell extract. The purified RNA also had a lighter band of lower molecular weight that ran below the TAPSO/MES buffer front, which is likely due to RNA degradation. Other procedures, using an extraction step that omitted the use of chloroform did not show the band.

Protein staining of the identical gel showed protein concentrated at both the TAPSO/MES front and the Bicine/TAPSO front. Clearly, the total purification of RNA needs to exclude protein and although some proteins are excluded from the RNA band resulting in a partial purification, a considerable amount of protein copurifies with the RNA. If removal of this protein content is critical, then a proteinase treatment similar to many other purification schemes that would result in reducing proteins to a small size so that they separate below the TAPSO/MES front in a similar location to the degraded nucleic acid observed in the phenol chloroform extracted RNA (lane 3). Such a proteinase treatment would be relatively quick and peptide purification from RNA post-proteinase treatment could likely be performed simultaneously with separation of RNA from other nucleic acids.

The invention demonstrates that RNA can be separated from other nucleic acids present in a cell extract and simultaneously concentrated by isotachophoresis at the interface of a buffer front. As described above, it has previously been shown that simultaneous concentration and purification of the bacterial genomic DNA and viral RNA using slightly different conditions can be optimized for these purposes, but with the same general approach and set-up. Therefore, an opportunity is created to have a single automated system that runs slightly different programs with different sets of disposables for all of these purposes.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are incorporated by reference in their entirety.

What is claimed is:

1. A method of simultaneously separating and concentrating nucleic acid and protein targets, the steps comprising:
 (i) obtaining a sample comprising a nucleic acid and a protein;
 (ii) adding said sample to a gel electrophoresis unit, said gel electrophoresis includes a gel box with a negative electrode side and a positive electrode side, the negative electrode side being filled with a first buffer comprising 2-Hydroxy-N-(tris(hydroxymethyl) methyl)-3-aminopropanesulfonic acid buffer and the positive electrode side being filled with a second buffer being different than said first buffer;
 (iii) subsequent to step (ii), subjecting said sample to isotachophoresis, said subjecting step comprising a step of applying a voltage to said gel electrophoresis unit; and
 (iii) subsequent to step (iii), detecting the presence of the nucleic acid and the protein.

2. The method of claim 1 wherein the detecting the presence of protein is selected from the group consisting of immunoassay, protein sequencing, mass spectrometry, functional assays, non-antibody ligand binding, aptamers, gels, and/or combinations thereof; and the detecting the presence of nucleic acid is selected from the group consisting of PCR, isothermal amplification methods, hybridization reactions, microarrays, protein-DNA binding, mass spectrometry, gels, and/or combinations thereof.

3. The method of claim 1 wherein the detecting the presence of protein is selected from the group consisting of immunoassay, protein sequencing, mass spectrometry, functional assays, non-antibody ligand binding, aptamers, gels, and/or combinations thereof; and the detecting the presence of nucleic acid is selected from the group consisting of PCR, isothermal amplification methods, hybridization reactions, microarrays, protein-DNA binding, mass spectrometry, gels, and/or combinations thereof, and wherein the detecting the presence of nucleic acid and protein are performed in a single output.

4. The method of claim 1 wherein subjecting said sample to isotachophoresis comprises simultaneously purifying and concentrating both the nucleic acid and the protein by driving the nucleic acid toward a positive electrode and driving the protein toward a negative electrode responsive to application of a voltage.

5. The method of claim 4 wherein the sample is subjected to isotachophoresis on a cartridge of a handheld device.

6. The method of claim 1 wherein subjecting said sample to isotachophoresis comprises simultaneously purifying and concentrating both the nucleic acid and the protein, the purifying being accomplished by driving the nucleic acid toward a positive electrode and driving the protein toward a negative electrode responsive to application of a voltage, the concentrating being simultaneously accomplished based on the first and second buffers causing separation of different nucleic acids or proteins while the different nucleic acids or proteins move in opposite directions so that different nucleic acids are separated from each other or different proteins are separated from each other while moving in respective opposite directions responsive to the application of a voltage based on respective different charges associated with the different nucleic acids or proteins in the buffer.

7. The method of claim 1 wherein the gel box contains a solidified gel matrix including a top surface, said negative electrode side being filled with said first buffer to a first buffer fill level being equal to or below said top surface of the solidified gel matrix and said positive electrode side being filled with said second buffer to a second buffer fill level being equal to or below said top surface of the solidified gel matrix.

* * * * *